United States Patent
Heuft (10) Patent No.: US 8,334,384 B2
(45) Date of Patent: Dec. 18, 2012

(54) PROCESS FOR PREPARING TETRAHYDROTETRAAZAPENTACENES AND DERIVATIVES

(75) Inventor: Matthew A. Heuft, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/977,187

(22) Filed: Dec. 23, 2010

(65) Prior Publication Data

US 2012/0165529 A1   Jun. 28, 2012

(51) Int. Cl.
*C07D 241/36* (2006.01)
(52) U.S. Cl. ..................................... 544/342
(58) Field of Classification Search ................ 544/342
See application file for complete search history.

*Primary Examiner* — Douglas M Willis
(74) *Attorney, Agent, or Firm* — Fay Sharpe LLP

(57) ABSTRACT

A process for preparing 5,7,12,14-tetrahydro-5,7,12,14-tetraazapentacene compounds and derivatives of Formula (A):

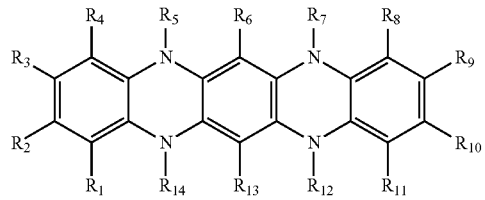

Formula (A)

comprises reacting at least one 1,2-diaminobenzene compound of Formula (I) with a 1,2,4,5-tetrahydroxybenzene compound of Formula (II):

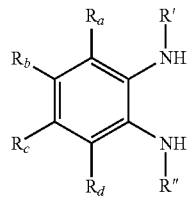

Formula (I)

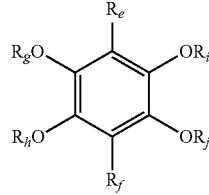

Formula (II)

wherein $R_1$-$R_{14}$, $R_a$-$R_j$, R', and R" are as described herein.

16 Claims, 2 Drawing Sheets

PROCESS FOR PREPARING TETRAHYDROTETRAAZAPENTACENES AND DERIVATIVES

CROSS REFERENCE TO RELATED PATENTS AND APPLICATIONS

This application is related to U.S. patent application Ser. No. 12/977,209, filed on Dec. 23, 2010. The disclosure of that application is hereby fully incorporated by reference herein.

BACKGROUND

The present disclosure relates to processes for preparing compounds known as tetrahydrotetraazapentacenes, and derivatives thereof. These pentacene analogues are particularly useful as semiconductors in electronic devices, such as thin-film transistors. These pentacene analogues have improved performance characteristics.

Pentacene is a commonly used semiconductor material in small organic semiconductors with high field-effect mobility.

Most small organic semiconductors with high field-effect mobility are based on pentacene. However, pentacene has poor solubility, requiring an expensive high vacuum deposition process to be used. Soluble pentacene derivatives are prone to oxidation in solution when exposed to air, preventing device fabrication from solution in ambient conditions. There is a need to develop new technologies to dramatically improve the mobility for broad applications.

There is a need to develop new processes for preparing pentacene analogues with improved properties.

BRIEF DESCRIPTION

The present disclosure relates to processes for preparing 5,7,12,14-tetrahydrotetraazapentacenes and derivatives which are useful as semiconductors or semiconducting materials.

Disclosed is a process for preparing a 5,7,12,14-tetrahydro-5,7,12,14-tetraazapentacene compound, comprising reacting at least one 1,2-diaminobenzene compound with a 1,2,4,5-tetrahydroxybenzene compound.

The at least one 1,2-diaminobenzene compound generally has the structure of Formula (I):

Formula (I)

wherein $R_a$, $R_b$, $R_c$, and $R_d$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen. R' and R" are independently selected from hydrogen, alkyl, substituted alkyl, aryl, substituted aryl.

In some embodiments, R' and R" are both hydrogen. In other embodiments, R' and R" are different from each other. In some additional embodiments, $R_b$ and $R_c$ are identical. In other embodiments, $R_a$ and $R_d$ are identical. In still others, $R_a$, $R_b$, $R_c$, and $R_d$ are identical.

The 1,2,4,5-tetrahydroxybenzene compound has the structure of Formula (II):

Formula (II)

wherein $R_e$ and $R_f$ are independently selected from the group consisting of hydrogen, alkyl, alkenyl, alkynyl, substituted alkyl, substituted alkenyl, substituted alkynyl, aryl, substituted aryl, and halogen; and $R_g$, $R_h$, $R_i$, and $R_j$ are independently selected from the group consisting of hydrogen, alkyl, and substituted alkyl.

In some embodiments, $R_e$ and $R_f$ are both hydrogen. In others, $R_e$ and $R_f$ are different from each other. In yet others, $R_e$ and $R_f$ are identical.

The at least one 1,2-diaminobenzene compound and the 1,2,4,5-tetrahydroxybenzene compound can be combined to form a mixture, and the mixture is then heated in an inert environment to form the 5,7,12,14-tetrahydro-5,7,12,14-tetraazapentacene compound. The mixture can be heated at a temperature of from about 110° C. to about 250° C., and the mixture can be heated for a time period of from about 30 minutes to about 12 hours.

Alternatively, the at least one 1,2-diaminobenzene compound and the 1,2,4,5-tetrahydroxybenzene compound can be combined to form a mixture, and the mixture is then heated in an inert environment to form the 5,7,12,14-tetrahydro-5,7,12,14-tetraazapentacene compound. The mixture can be heated at a temperature above 300° C., and the mixture can be heated for a time period of from about 30 seconds to about 10 minutes.

Alternatively, the at least one 1,2-diaminobenzene compound and the 1,2,4,5-tetrahydroxybenzene compound are dissolved in a solvent to form a solution, and the solution is heated to form the 5,7,12,14-tetrahydro-5,7,12,14-tetraazapentacene compound. The solution can be heated at a temperature of from about 80° C. to about 180° C., and the solution can be heated for a time period of from about 30 minutes to about 12 hours.

The solvent can be a carboxylic acid such as acetic acid, methanoic acid, ethanoic acid, octadecanoic acid, propanoic acid, benzenecarboxylic acid, propanedioic acid, butanedioic acid, and the like, and combinations thereof; or a polar, aprotic solvent such as NMP, DMF, DMA, DMSO, and the like, and combinations thereof.

The process may further comprise isolating the 5,7,12,14-tetrahydro-5,7,12,14-tetraazapentacene compound, washing, and drying the 5,7,12,14-tetrahydro-5,7,12,14-tetraazapentacene compound.

The molar ratio of the at least one 1,2-diaminobenzene compound to the 1,2,4,5-tetrahydroxybenzene compound is from 2:1 to about 2.5:1.

In some particular embodiments, one molar unit of the 1,2,4,5-tetrahydroxybenzene compound is reacted with about one molar unit of a first 1,2-diaminobenzene compound to form an intermediate, and the intermediate is subsequently reacted with about one molar unit of a second 1,2-diaminobenzene compound to form the 5,7,12,14-tetrahydro-5,7,12,14-tetraazapentacene compound. The first 1,2-diaminobenzene compound and the second 1,2-diaminobenzene compound are different.

Also disclosed in embodiments is a process for preparing an 5,7,12,14-tetrasubstituted-5,7,12,14-tetraazapentacene, comprising reacting 5,7,12,14-tetrahydro-5,7,12,14-tetraazapentacene (TH-TAP) with a sidechain-producing reagent that is selective for nitrogen atoms. The sidechain-producing reagent may have the structure of Formula (B), as described further herein.

In some embodiments, the TH-TAP and the sidechain-producing reagent react to form an intermediate. The process then further comprises reducing the intermediate to obtain the 5,7,12,14-tetrasubstituted-5,7,12,14-tetraazapentacene.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The present disclosure relates to processes for preparing 5,7,12,14-tetrahydro-5,7,12,14-tetraazapentacene compounds and derivatives. Those compounds are generally of Formula (A):

Formula (A)

wherein each of $R_1$, $R_2$, $R_3$, $R_4$, $R_6$, $R_8$, $R_9$, $R_{10}$, $R_{11}$, and $R_{13}$ is independently selected from hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen; and each of $R_5$, $R_7$, $R_{12}$, and $R_{14}$ are independently selected from hydrogen, alkyl, substituted alkyl, alkenyl, substituted alkenyl, alkynyl, substituted alkynyl, aryl, substituted aryl, heteroaryl, substituted heteroaryl, acyl, and arylalkyl. The "tetrahydro" portion of the nomenclature indicates that a substituent is present on each nitrogen atom.

Generally, these compounds can be formed by a process comprising reacting two molar units of at least one 1,2-diaminobenzene compound of Formula (I) with one molar unit of a 1,2,4,5-tetrahydroxybenzene compound of Formula (II):

Formula (I)

Formula (II)

wherein $R_a$, $R_b$, $R_c$, $R_d$, $R_e$, and $R_f$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen; and R' and R" are independently selected from the group consisting of hydrogen, alkyl, substituted alkyl, aryl, and substituted aryl; and $R_g$, $R_h$, $R_i$, and $R_j$ are independently selected from the group consisting of hydrogen, alkyl, and substituted alkyl.

The term "alkyl" refers to a substituent composed entirely of carbon atoms and hydrogen atoms which is fully saturated, can be linear or branched, and is of the formula —$C_nH_{2n+1}$.

The term "alkenyl" refers to a substituent which contains at least one carbon-carbon double bond that is not part of an aromatic ring. The substituent may be linear, branched, or cyclic. Exemplary alkenyl substituents include ethenyl (—CH=CH$_2$) and phenylvinyl (—CH=CH—C$_6$H$_5$).

The term "alkynyl" refers to a substituent which contains at least one carbon-carbon triple bond that is not part of an aromatic ring. The substituent may be linear, branched, or cyclic. A triple bond is not considered a double bond, and a double bond is not considered a triple bond. A substituent which contains a double bond and a triple bond should be considered an alkynyl substituent and not an alkenyl substituent. Exemplary alkynyl substituents include phenylacetylenyl (—C≡C—C$_6$H$_5$).

The term "aryl" refers to an aromatic substituent composed entirely of carbon atoms and hydrogen atoms. When aryl is described in connection with a numerical range of carbon atoms, it should not be construed as including aromatic substituents which are substituted. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to an aromatic substituent composed of carbon atoms, hydrogen atoms, and one or more heteroatoms. The carbon atoms and the heteroatoms are present in a cyclic ring or backbone of the substituent. The heteroatoms are selected from O, S, and N. Exemplary heteroaryl substituents include thienyl, pyridinyl, and imidazolyl.

The term "ketonyl" refers to a substituent having a carbon atom double-bonded to an oxygen atom and single bonded to an alkyl or substituted alkyl group, i.e. —(C=O)—R. An exemplary ketonyl substituent is methylcarbonyl (—COCH$_3$).

The term "arylalkyl" refers to an aromatic substituent which is connected to an alkylene substituent. An alkylene substituent is composed of carbon atoms which are fully saturated, and has the ability to form a single bond with two different atoms. Arylalkyl groups can also be substituted. Exemplary arylalkyl substituents include benzyl (—CH$_2$—C$_6$H$_5$).

The term "substituted" refers to at least one hydrogen atom on the named substituent being substituted with another functional group selected from the group consisting of halogen —OH, —CN, —NO$_2$, —COOH, —SO$_3$H, and SiR$_3$ wherein R is alkyl. An exemplary substituted alkyl group is a perhaloalkyl group, wherein one or more hydrogen atoms in an alkyl group are replaced with halogen atoms, such as fluorine, chlorine, iodine, and bromine. An aryl or heteroaryl group may be substituted with the above-listed functional groups and with alkyl or alkoxy as well. Exemplary substituted aryl groups include methylphenyl (CH$_3$—C$_6$H$_4$—) and methoxyphenyl. Exemplary substituted heteroaryl groups include dodecylthienyl.

Generally, the alkyl, alkenyl, and alkynyl groups each independently contain from 1 to 30 carbon atoms. Similarly, the aryl groups independently contain from 6 to 30 carbon atoms.

In specific embodiments of the tetrahydroxybenzene compound of Formula (II), $R_g$ and $R_j$ are the same, $R_h$ and $R_i$ are the same, and $R_i$ and $R_j$ are different from each other.

A tetrahydroxybenzene of Formula (II) can be produced, for example, by the reduction of a 2,5-dihydroxy-1,4-benzoquinone, as shown below in Scheme 1:

Scheme 1

In some embodiments, the reaction occurs by heating a solid mixture of the two starting materials of Formulas (I) and (II) in an inert atmosphere, such as nitrogen (N$_2$) or argon.

In other embodiments, the diaminobenzene of Formula (I) and the tetrahydroxybenzene of Formula (II) are dissolved in a solvent and heated.

In embodiments, the diaminobenzene compound and tetrahydroxybenzene compound are heated at a temperature above 300° C., including from about 300° C. to about 500° C., including about 300° C. to about 450° C. for a period of time between about 30 seconds and about 10 minutes when mixed in the absence of a solvent. Such heating can be accomplished using a torch. Alternatively, the diaminobenzene compound and tetrahydroxybenzene compound are heated at a temperature between about 110° C. and about 250° C., including from about 150° C. to about 200° C. for a period of time between about 30 minutes and about 12 hours, when mixed in the absence of a solvent. When dissolved in a solvent, the diaminobenzene compound and tetrahydroxybenzene compound are heated at a temperature between about 80° C. and about 110° C. The diaminobenzene compound and tetrahydroxybenzene compound are heated for a period of time between about 30 minutes and about 12 hours. This heating can be done in an oven, for example.

As noted above, the diaminobenzene compound and tetrahydroxybenzene compound can be dissolved in a solvent prior to heating. Exemplary solvents include carboxylic acids such as acetic acid, methanoic acid, ethanoic acid, octadecanoic acid, propanoic acid, (Z)-9-octadecanoic acid, benzenecarboxylic acid, propanedioic acid, butanedioic acid, and the like, and combinations thereof; and polar, aprotic solvents such as NMP, DMF, DMA, DMSO, and the like, and combinations thereof.

After reaction, the tetraazapentacene compound can be washed with acetone or a variety of other solvents such as methanol, toluene, THF, and diethyl ether; and dried, for example in a vacuum oven. The drying typically occurs at a temperature of about 60° C. for a period of from about 8 hours to about 12 hours. The product can be further purified by sublimation or acid pasting.

In particular embodiments, $R_a$, $R_b$, $R_c$, $R_d$, $R_e$, $R_f$, $R_g$, $R_h$, $R_i$, $R_j$, R', and R" are all hydrogen. In these embodiments, the diaminobenzene compound is of formula (1) and the tetrahydroxybenzene compound is of formula (2):

Formula (1)

Formula (2)

Here, the resulting tetrahydrotetraazapentacene compound is 5,7,12,14-tetrahydro-5,7,12,14-tetrahydroazapentacene, which may be abbreviated as TH-TAP and is shown in Formula (3):

Formula (3)

Derivatives of TH-TAP may also be desirable. For example, substitutions on the A and E rings, i.e. the terminal phenyl rings, may aid solubility, extend the chromophore to tune the semiconductor properties, and/or affect the solid state packing. These substitutions occur when at least one of $R_a$, $R_b$, $R_c$, and $R_d$ in the compound of Formula (I) is not hydrogen. In particular embodiments, at least one of $R_a$, $R_b$, $R_c$, and $R_d$ is selected from alkyl, aryl, alkenyl, and alkynyl.

In other embodiments, the nitrogen atoms are substituted. Such a substitution may aid solubility, extend the chromophore to tune the semiconductor properties, affect the solid state packing, and/or improve the oxidative stability of the compound. These substitutions occur when at least one of R' and R" is not hydrogen. In particular embodiments, at least one of R' and R" is selected from substituted alkyl and substituted aryl.

Substitutions on the C ring, i.e. the internal phenyl ring, may also be desirable. These substitutions occur when at least one of $R_e$ and $R_f$ in the compound of Formula (II) is not hydrogen. In particular embodiments, at least one of $R_e$ and $R_f$ is selected from alkyl, aryl, alkenyl, and alkynyl.

Symmetrical tetrahydrotetraazapentacene derivatives can be prepared using two equivalents of the diaminobenzene compound of Formula (I) to react with the tetrahydroxybenzene compound of Formula (II), as illustrated in Reaction (1) below:

Reaction (1)

Reactions (2) and (3) may be utilized when different substitutions on the A and E rings are desired. First, as shown in Reaction (2), one equivalent of a first diaminobenzene is reacted with the tetrahydroxybenzene. Put another way, the molar ratio of the first diaminobenzene compound and the tetrahydroxybenzene compound is about 1:1.

Reaction (2).

Next, in Reaction (3), the intermediate product produced in Reaction (2) is reacted with a second diaminobenzene compound. The second diaminobenzene compound is different from the first diaminobenzene compound.

Reaction (3).

In Reaction (4), the C ring is substituted, i.e. one or both of $R_e$ and $R_f$ is not hydrogen. This result can be achieved by appropriate substitutions on the tetrahydroxybenzene compound.

Reaction (4)

In Reaction (5), one or more of the nitrogen atoms of the B and/or D rings is substituted. This result can be achieved by substituting one or both of the amine groups of the diaminobenzene.

Reaction (5)

When the nitrogen atom substituents are the same, symmetrical B and D ring derivatives are prepared. When the nitrogen atom substituents are different, a mixture of unsymmetrical regioisomers is prepared.

The concepts of the above Reactions (1)-(5) may be combined to produce compounds with substitutions at every position on the tetraazapentacene framework. Depending on the compound to be produced, adding a molar excess of the diaminobenzene compound ensures completion of the reaction. In embodiments, the molar ratio of the at least one diaminobenzene compound to the tetrahydroxybenzene compound is from 2:1 to about 2.5:1.

Compounds having substituents on the nitrogen atoms of the B and/or D rings can also be prepared by functionalizing TH-TAP. Generally speaking, N-substituted compounds of Formula (A) are formed by reacting TH-TAP with a sidechain-producing reactant to obtain an N-substituted TH-TAP compound. The sidechain-producing reactant reacts selectively with the nitrogen atoms, rather than any of the carbon atoms in the A, C, or E rings. For example, as shown in Reactions (6), (7), (8), and (9), N-substituted compounds can be obtained by an alkylation or cross-coupling reaction:

wherein in Reactions (6)-(8) each R is independently alkyl, substituted alkyl, aryl, substituted aryl, heteroaryl, or substituted heteroaryl, and in Reaction (9) R may also be trialkylsilyl. Please note the overall substituent on the nitrogen atom of Reaction (8) would be considered an alkenyl or substitutent alkenyl substituent. The overall substituent on the nitrogen atom of Reaction (9) would be considered an alkynyl or substituted alkynyl substituent.

Generally, the sidechain-producing reactant is of Formula (B):

$$X\text{-}L\text{-}R_{15} \qquad \text{Formula (B)}$$

where X is halogen or hydrogen; $R_{15}$ is selected from alkyl, substituted alkyl, alkenyl, substituted alkenyl, alkynyl, substituted alkynyl, aryl, substituted aryl, heteroaryl, substituted heteroaryl, acyl, and arylalkyl; and L is a divalent linkage. The term "divalent linkage" refers to any moiety which is able to form a single bond with two different atoms, joining those two different atoms together. Exemplary divalent linkages that may be useful in Formula (B) include carbonyl (—C(=O)—), a single bond (i.e. the formula collapses into X—$R_{15}$), ethenyl (—CH=CH—), and acetylenyl (—C≡C—).

In some embodiments, the sidechain-producing reactant is reduced to obtain the N-substituted TH-TAP compound. For example, in Reaction (10), TH-TAP is reacted with an acid chloride, which can provide N-substituted compounds having a acyl substituent. The resulting intermediate can be be reduced, if desired, to obtain alkyl or substituted alkyl substituents. Any suitable reducing agent may be used; LiAlH$_4$ is merely exemplary.

Reaction (10)

or

N-substituted compounds with different substituents can be made by performing Reactions (6)-(10) sequentially with an excess of the TH-TAP compound compared to the sidechain-producing reagent, as desired.

The compounds of the present disclosure exhibit high mobility, great solubility, and good oxidative stability. The compounds are particularly suitable for electronic devices, in particular thin-film transistors. More particularly, the compounds are suitable for use as semiconductor materials in printed organic electronics.

The compounds exhibit air stability of months in the solid state and weeks in solution, compared to pentacene's air stability of minutes.

The following examples illustrate electronic devices made according to the methods of the present disclosure. The examples are merely illustrative and are not intended to limit the present disclosure with regard to the materials, conditions, or process parameters set forth therein. All parts are percentages by weight unless otherwise indicated.

EXAMPLES

Example 1

TH-TAP was prepared. 1,2-diaminobenzene (8.37 grams, 77 mmol, 2.2 equivalents) and 1,2,4,5-tetrahydroxybenzene (5 grams, 35.2 mmol, 1 equivalent) were ground together using a mortar and pestle and transferred to an amber jar and purged with argon. The jar was sealed and placed in a 180° C. bath for 1 hour. The material never dissolved. The material was heated with a propane torch for 5 to 10 minutes. The crude material was collected by filtration and washed with acetone. Soxhlet extraction of the solid (tetrahydrofuran, 1,2-dichlorobenzene) did not afford much material. Dimethyl sulfoxide (DMSO) extracts afforded some purple solid. Ethanol extracts afforded very little material.

The purple solid was recovered from the soxhlet thimble and dried in a vacuum oven. Train vacuum sublimation with a first zone at 360° C. and a second zone at 340° C. afforded a metallic green solid.

Figure 1:
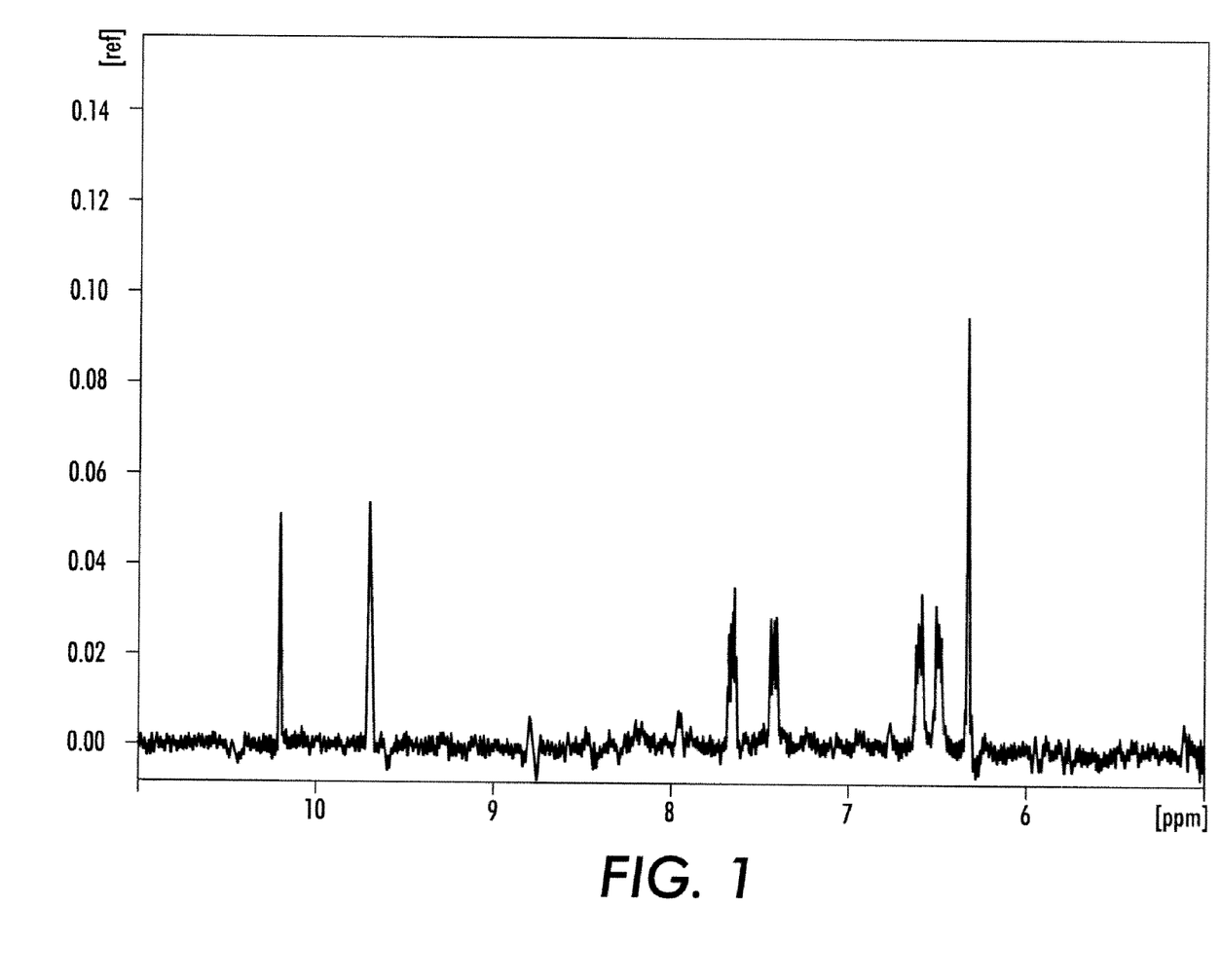
FIG. 1 is a $^1$H nuclear magnetic resonance spectrum of a compound produced using an exemplary process of the present disclosure.

Proton nuclear magnetic resonance spectroscopy, i.e. $^1$H NMR, was conducted at a frequency of 300 MHz after dissolving metallic green solid in DMSO-d6. The solution was fluorescent reddish-pink. The signal was weak and the $^1$H NMR spectrum (FIG. 1) showed aromatic protons at chemical shifts below and above 7 ppm Differential scanning calorimetry (DSC) was conducted and showed no thermal event below 350° C. Thermal gravimetric analysis was also conducted and showed less than 1% loss at 300° C. and about 4% loss at 450° C. Major product loss started at about 550° C. These results indicate the high thermal stability of these compounds.

The calculated elemental analysis for a 100% pure 5,7,12,14-tetrahydro-5,7,12,14-tetraazapentacene ($C_{18}H_{14}N_4$) is 75.5 wt % carbon, 4.93 wt % hydrogen, and 19.57 wt % nitrogen. The observed sample included 75.2 wt % carbon, 4.2 wt % hydrogen, and 19.9 wt % nitrogen.

Figure 2:
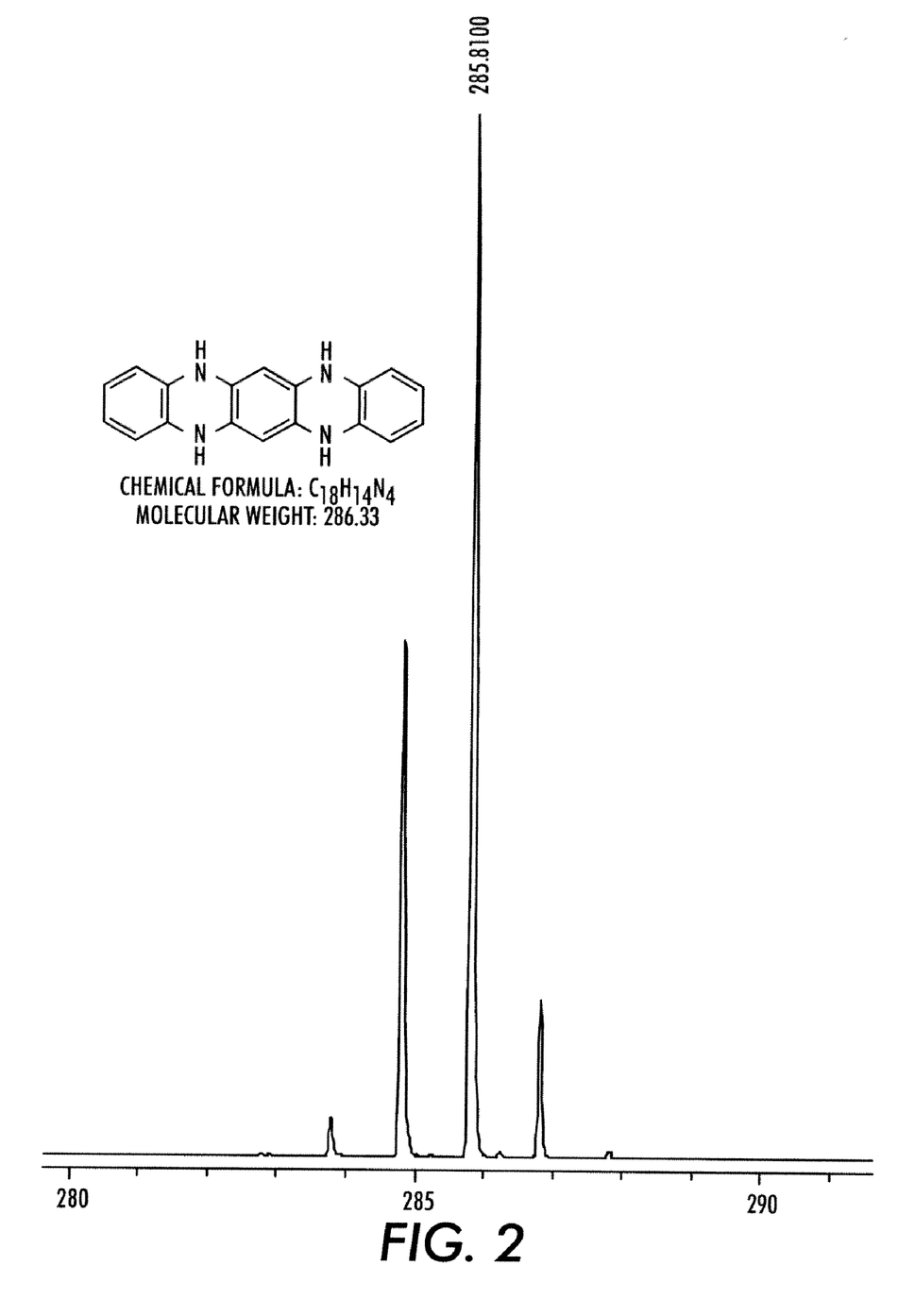
FIG. 2 is a high resolution mass spectrometry spectrum of a compound produced using an exemplary process of the present disclosure.

Matrix-assisted laser desorption/ionization was performed using a time-of-flight mass spectrometer (MALDI-TOF). The calculated mass of 5,7,12,14-tetrahydrotetraazapentacene is 286.1218 Da. The observed mass using MALDI-TOF was 285.8100. FIG. 2 is the MALDI-TOF spectrum.

Example 2

TH-TAP can also be prepared as described below. 1,2-Phenylene diamine (799 milligrams, 7.39 mmol, 2.1 eq) and pyrocatechol (500 mg, 3.52 mmol, 1 eq) were ground together using a mortar and pestle and transferred to an amber jar and purged thoroughly with Argon. The amber jar was clamped by the lid and heated in an oven at 180° C. for 4 hours. A green residue was present on the side of the vial with a dark (black) residue at the bottom. The sample was purified by train vacuum sublimation with a first zone (sample) at 360° C. and a second zone at 340° C. to afford a metallic green solid.

Example 3

2,3,9,10-tetramethyl-5,7,12,14-tetrahydrotetraazapentacene was prepared. This compound is illustrated as Formula (4) below:

Formula (4)

1,2,4,5-tetrahydroxybenzene (2.0 grams, 14.1 mmol) and 4,5-dimethyl-1,2-phenylenediamine (3.83 grams, 28.2 mmol) were ground together with a mortar and pestle, and placed in a tightly sealed vial under an argon atmosphere. The vial was heated in a 180° C. oven for 4 hours, then opened to air and allowed to cool. The resulting material was washed with acetone several times, filtered, and dried.

A portion (2 grams) of the isolated sample was slowly added to trifluoroacetic acid (175 mL) over a 30 minute period and allowed to dissolve for 45 minutes. The resulting solution was filtered to remove insoluble impurities. The filtrate (a dark blue mixture) was added slowly to ice-cold deionized water (700 mL). The resulting precipitate was collected by filtration, reslurried in deioized water, filtered, and dried in a vacuum oven at 50° C. to afford the product as a black-purple solid (1.52 grams).

Example 4

9,10-dimethyl-5,7,12,14-tetrahydroazapentacene was prepared. This compound is illustrated as Formula (5) below:

Formula (5)

1,2-Phenylene diamine (761 mg, 7.04 mmol, 1 eq) and 1,2,4,5-tetrahydroxybenzene (1.00 grams, 7.04 mmol, 1 eq) were ground together using a mortar and pestle and transferred to an amber jar and purged thoroughly with Ar. The jar was sealed and placed in a 180° C. oven for 3 hours. The jar was cooled to room temperature and the material was blended with 4,5-dimethylphenylenediamine (958 mg, 7.04 mmol, 1 eq) in a mortar and pestle. The jar was purged with Argon, sealed, and placed in a 180° C. oven for 3 hours. The sample was removed from the oven and cooled to room temperature. The sample was a mass of black (shimmery green) solid. The sample weighed 2.03 grams indicating a yield of 92%.

Example 5

A compound of Formula (6) was prepared:

Formula (6)

1,2,4,5-tetrahydroxybenzene (158 mg, 1.11 mmol, 1.0 eq.) was ground to a fine powder using a mortar and pestle and then added to a glass vial containing N,N'-dimethyl-o-phenylenediamine (303 mg, 2.22 mmol, 2.0 eq.). The vial was flushed thoroughly with argon, sealed, and then heated slightly under a flame gun to make a homogeneous solid. The reaction was heated to 180° C. for 4 hours to afford a brown solid.

Example 6

A compound of Formula (7) was prepared:

Formula (7)

A four-dram vial was equipped with a magnetic stir bar. DMA (2 mL) and water (2 mL) were placed in the vial and Argon was bubbled through the solvent for 1 hour. PdCl$_2$(t-Bu$_2$PhP)$_2$ (12 milligrams, 20 µmol, 0.05 mol %) was added to the vial which resulted in an orange, heterogeneous solution. Bromobenzene (548 mg, 3.5 mmol, 10 eq) was added and the resulting two-phase solution (orange on the bottom) was stirred under Argon for 5 minutes. TH-TAP (100 mg, 350 µmol, 1 eq) was added and the suspension was stirred under Argon for 5 min. NaOH (210 mg, 5.24 mmol, 15 eq) was added and the vial was sealed. The reaction turned a dark blue color and was heated to 100° C. (hot plate set temperature was 115° C.). The reaction was left for 4 hours, then cooled to 22° C. The sample was poured into THF (10 mL) and washed with NH4Cl (sat. aq., 3×10 mL). The organic phase was concentrated to afford the product. Standard purification methods were used to isolate and purify the product. The general reaction is shown below:

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A process for preparing a 5,7,12,14-tetrahydro-5,7,12,14-tetraazapentacene compound of Formula (A):

Formula (A)

wherein each of $R_1$, $R_2$, $R_3$, $R_4$, $R_6$, $R_8$, $R_9$, $R_{10}$, $R_{11}$, and $R_{13}$ is independently selected from hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen; and each of $R_5$, $R_7$, $R_{12}$, and $R_{14}$ are independently selected from hydrogen, alkyl, substituted alkyl, alkenyl, substituted alkenyl, alkynyl, substituted alkynyl, aryl, substituted aryl, heteroaryl, substituted heteroaryl, acyl, and arylalkyl;

comprising reacting at least one compound of Formula(I):

Formula (I)

wherein $R_a$, $R_b$, $R_c$, and $R_d$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen; and wherein R' and R" are independently selected from the group consisting of hydrogen, alkyl, substituted alkyl, aryl, and substituted aryl;

with a compound of Formula (II):

Formula (II)

wherein $R_e$ and $R_f$ are independently selected from the group consisting of hydrogen, alkyl, alkenyl, alkynyl, substituted alkyl, substituted alkenyl, substituted alkynyl, aryl, substituted aryl, and halogen; and $R_g$, $R_h$, $R_i$, and $R_j$ are independently selected from the group consisting of hydrogen, alkyl, and substituted alkyl.

2. The process of claim 1, wherein the at least one compound of Formula (I) and the compound of Formula (II) are mixed together to form a mixture, and the mixture is heated in an inert environment to form the compound of Formula (A).

3. The process of claim 2, wherein the mixture is heated at a temperature of from 110° C. to 250° C.

4. The process of claim 3, wherein the mixture is heated for a period of from 30 minutes to 12 hours.

5. The process of claim 2, wherein the mixture is heated at a temperature above 300° C. for a period of from 30 seconds to 10 minutes.

6. The process of claim 1, wherein the at least one compound of Formula (I) and the compound of Formula (II) are dissolved in a solvent to form a solution, and the solution is heated to form the compound of Formula (A).

7. The process of claim 6, wherein the solution is heated at a temperature of from 80° C. to 180° C.

8. The process of claim 6, wherein the solution is heated for a period of from 30 minutes to 12 hours.

9. The process of claim 6, wherein the solvent is methanoic acid, ethanoic acid, octadecanoic acid, propanoic acid, benzenecarboxylic acid, propanedioic acid, butanedioic acid, N-methyl pyrrolidone, dimethylformamide, dimethylacetamide, or dimethylsulfoxide.

10. The process of claim 1, wherein R' and R" are both hydrogen.

11. The process of claim 1, wherein R' and R" are identical to each other.

12. The process of claim 1, wherein $R_b$ and $R_c$ are identical.

13. The process of claim 1, further comprising:
isolating the 5,7,12,14-tetrahydro-5,7,12,14-tetraazapentacene compound of Formula (A),
washing the 5,7,12,14-tetrahydro-5,7,12,14-tetraazapentacene compound of Formula (A), and
drying the 5,7,12,14-tetrahydro-5,7,12,14-tetraazapentacene compound of Formula (A).

14. The process of claim 1, wherein the molar ratio of the at least one compound of Formula (I) to the compound of Formula (II) is from 2:1 to 2.5:1.

15. The process of claim 1, wherein one molar unit of the compound of Formula (II) is reacted with one molar unit of a first compound of Formula (I) to form an intermediate:

wherein $R_p$ is independently selected from the group consisting of hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen;

and the intermediate is subsequently reacted with one molar unit of a second compound of Formula (I) to form the 5,7,12,14-tetrahydro-5,7,12,14-tetraazapentacene compound of Formula (A), wherein the first compound of Formula (I) and the second compound of Formula (I) are different.

16. A process for preparing an 5,7,12,14-tetrasubstituted-5,7,12,14-tetraazapentacene of Formula (A):

Formula (A)

wherein each of $R_1$, $R_2$, $R_3$, $R_4$, $R_6$, $R_8$, $R_9$, $R_{10}$, $R_{11}$, and $R_{13}$ is independently selected from hydrogen, alkyl, substituted alkyl, alkenyl, substituted alkenyl, alkynyl, substituted alkynyl, aryl, substituted aryl, heteroaryl, substituted heteroaryl, acyl, arylalkyl, and halogen; and each of $R_5$, $R_7$, $R_{12}$, and $R_{14}$ are independently selected from hydrogen, alkyl, substituted alkyl, alkenyl, substituted alkenyl, alkynyl, substituted alkynyl, aryl, substituted aryl, heteroaryl, substituted heteroaryl, acyl, and arylalkyl;

comprising reacting a 5,7,12,14-tetrahydro-5,7,12,14-tetraazapentacene of Formula (3):

Formula (3)

with a sidechain-producing reagent of Formula (B):

X-L-R$_{15}$ where X is halogen or hydrogen; R$_{15}$ is selected from alkyl, substituted alkyl, alkenyl, substituted alkenyl, alkynyl, substituted alkynyl, aryl, substituted aryl, heteroaryl, substituted heteroaryl, acyl, and arylalkyl; and L is a divalent linkage selected from carbonyl, ethenyl, or acetylenyl.

\* \* \* \* \*